(12) United States Patent
Wolff

(10) Patent No.: US 8,109,898 B2
(45) Date of Patent: Feb. 7, 2012

(54) DEVICE FOR CONTROLLING THE OPENING AND CLOSING OF A CLAMP IN A POSITIVE DISPLACEMENT PUMP

(75) Inventor: Remy Wolff, Morette (FR)

(73) Assignee: Fresenius Vial SAS, Brèzins (FR)

( * ) Notice: Subject to any disclaimer, the term of this patent is extended or adjusted under 35 U.S.C. 154(b) by 266 days.

(21) Appl. No.: 12/513,785

(22) PCT Filed: Oct. 26, 2007

(86) PCT No.: PCT/EP2007/061548
§ 371 (c)(1),
(2), (4) Date: May 6, 2009

(87) PCT Pub. No.: WO2008/055793
PCT Pub. Date: May 15, 2008

(65) Prior Publication Data
US 2010/0040481 A1    Feb. 18, 2010

(30) Foreign Application Priority Data
Nov. 8, 2006 (FR) ..................................... 06 09742

(51) Int. Cl.
*A61M 31/00* (2006.01)
(52) U.S. Cl. ........................................................ 604/65
(58) Field of Classification Search ...................... 604/65
See application file for complete search history.

(56) References Cited

U.S. PATENT DOCUMENTS

| | | | |
|---|---|---|---|
| 6,261,262 B1 | 7/2001 | Briggs et al. | |
| 6,558,347 B1 | 5/2003 | Jhuboo et al. | |
| 6,629,955 B2 * | 10/2003 | Morris et al. | 604/153 |
| 2005/0020978 A1 * | 1/2005 | Vollenweider | 604/151 |

FOREIGN PATENT DOCUMENTS

| | | |
|---|---|---|
| EP | 1031358 A1 | 8/2000 |
| WO | 93/05829 A1 | 4/1993 |
| WO | 98/56453 A1 | 12/1998 |
| WO | 03/041787 A2 | 5/2003 |

OTHER PUBLICATIONS

International Search Report of PCT/EP2007/061548, date of mailing Feb. 5, 2008.

* cited by examiner

*Primary Examiner* — Nicholas Lucchesi
*Assistant Examiner* — Jason Flick
(74) *Attorney, Agent, or Firm* — Westerman, Hattori, Daniels & Adrian, LLP

(57) ABSTRACT

A device for controlling the opening and closing of a clamp intended to seal a flexible tube, for example in a positive displacement pump, includes: a housing that can be closed with a door; a tube placed inside the housing; a clamp also placed in the housing, which cooperates with the tube to open or seal it. The clamp is closed when the door is being opened and when the door is being closed. As well as ensuring that the tube is always closed when the door is being opened, the inventive safety device also ensures that the tube remains closed once the door has been closed as long as a suitable device does not trigger the opening of the clamp. The fully mechanical closure device is not exposed to the dangers of a faulty power supply.

30 Claims, 5 Drawing Sheets

Figure 1:
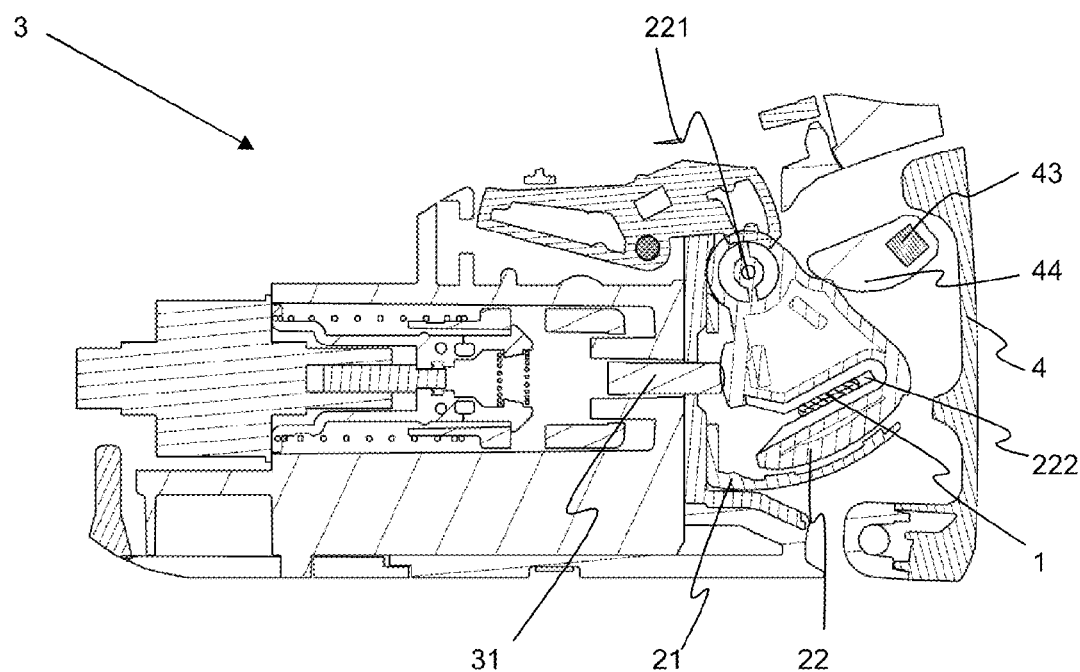

DEVICE FOR CONTROLLING THE OPENING AND CLOSING OF A CLAMP IN A POSITIVE DISPLACEMENT PUMP

The invention relates to a method for controlling the opening and closing of a clamp intended to seal a flexible tube placed inside a housing that can be closed with a door, the clamp being placed in the housing and cooperating with the tube in order to open and seal it. The invention also relates to a device for controlling the opening and closing of a clamp intended to seal a flexible tube, in particular, in a positive displacement pump comprising, among other things, a housing that can be closed with a door, a tube placed inside the housing, and a clamp placed inside the housing and cooperating with the tube in order to open and seal it.

In the field of perfusion, a tube connecting a medication source to a patient via a positive displacement pump should never be open without controlling the flow rate.

Perfusion systems are generally composed of a positive displacement pump contained in a housing closed by a door, with a flexible tube going through the housing via the pump. In order to prevent the liquid to be perfused from starting to flow before the tube is fitted in the pump, it is common practice to place a clamp downstream of the pump. This clamp is preferably closed the whole time the tube is being positioned in the pump, and then opened at the moment perfusion begins. There can also be a roller clamp upstream of the pump.

In this context it is common practice to equip the system with means for closing the clamp as soon as the door opens and means for opening the clamp as soon as the door closes. To cite an example, in application EP 0 238 227 A2, a slide clamp is opened and closed by a member associated with the handle of the pump housing door. The same principle is found in the device in document EP 1 218 055 A1, associated with a compression clamp in this case.

However, the latter function can present a hazard, particularly if the tube is not placed correctly in the pump or if the pump has a defect. In this case, an uncontrolled flow of the perfusion liquid toward the patient could occur, with all the associated risks.

In addition, from application EP 1 031 358 A1, a pump system is known in which means are provided to close the tube when the pump is already on and the tube is placed in the pump, making it possible to monitor the integrity of the system. In this case, the clamp is closed electrically while the door is closed. However, this system has many disadvantages. If the pump is off, if the battery is too weak, or if the motor for closing the clamp is out of order, for example, then the clamp cannot be closed. Furthermore, there is no way to close the clamp in a targeted manner when the pump door is activated.

The objective of the invention is to develop a safety method and device of the aforementioned type that, irrespective of battery status, whether the pump is on or off, and whether the tube is positioned correctly in the pump, makes it possible to prevent an uncontrolled flow of the perfusion liquid in the tube, even after the pump door is closed.

This objective is achieved according to the invention by the method and the device of the invention. To this end, the method involves closing the clamp when the door is made to close. In the device, the safety system additionally comprises means for closing the clamp when the door is made to close. These means make it possible to close the clamp if it is in open position, while leaving it closed if it is already in this position. This way, the perfusion liquid cannot flow freely after the door is closed.

A preferred embodiment of the invention involves closing the clamp when the door is made to open as well. To this end, the control device is equipped with means for closing the clamp when the door is made to open.

Preferably, the means for closing the clamp when the door is made to open and the means for closing the clamp when the door is made to close are identical. In this way, the same means will make the clamp close both at the moment the door opens and at the moment it closes.

In a preferred embodiment of the invention, the means for closing the clamp when the door is made to open and/or the means for closing the clamp when the door is made to close are activated by means for making the door open or close. For example, in an embodiment, the means for opening or closing the door comprise a handle that is operable from the outside of the housing.

A simple solution consists in designing means for closing the clamp when the door is made to open and/or means for closing the clamp when the door is made to close in the form of a cam able to cooperate with the means for opening or closing the door. The cam is preferably integral with the handle pivot pin.

For the clamp, one could use a sliding clamp, for example, commonly called a "slide clamp", made up of a stationary part and a mobile part, preferably with rotational mobility, with the means for closing the clamp when the door is made to open and the means for closing the clamp when the door is made to close being proportioned so as to make the mobile part of the slide clamp slide with respect to the stationary part.

It is preferable to provide means for making the clamp open after the door has been closed. To this end, control means can be provided for activating the clamp opening means when a certain event has occurred. This event can be the completion of a system integrity test, for example.

In order to prevent the clamp from being opened at the precise moment when the door is made to open, it is preferable to provide a mechanical fuse in order to deactivate the clamp opening means in the event that the door is made to open at the moment the opening means are activated.

This safety device is particularly intended for a positive displacement pump connected to the tube, preferably a peristaltic pump, with the positive displacement pump preferably being placed upstream of the clamp.

Figure 2:
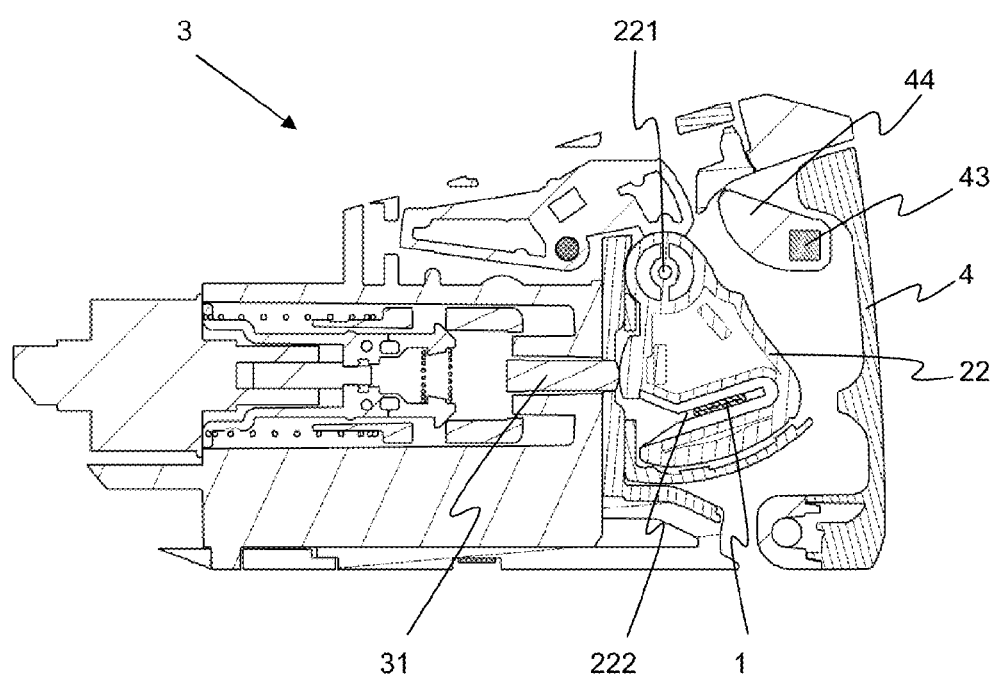
Figure 3:
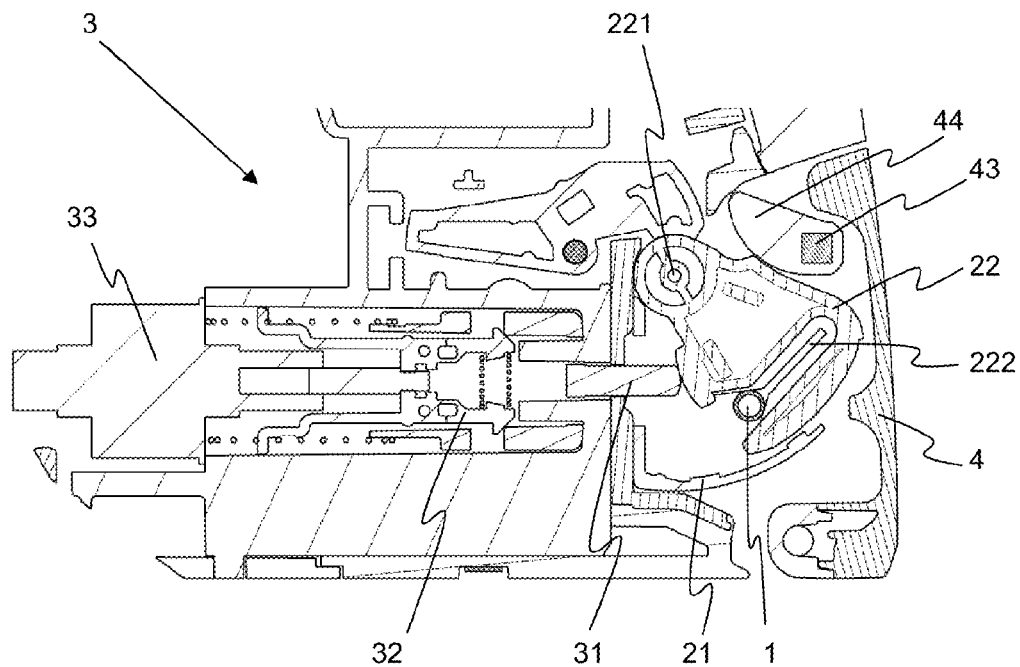
Figure 4:
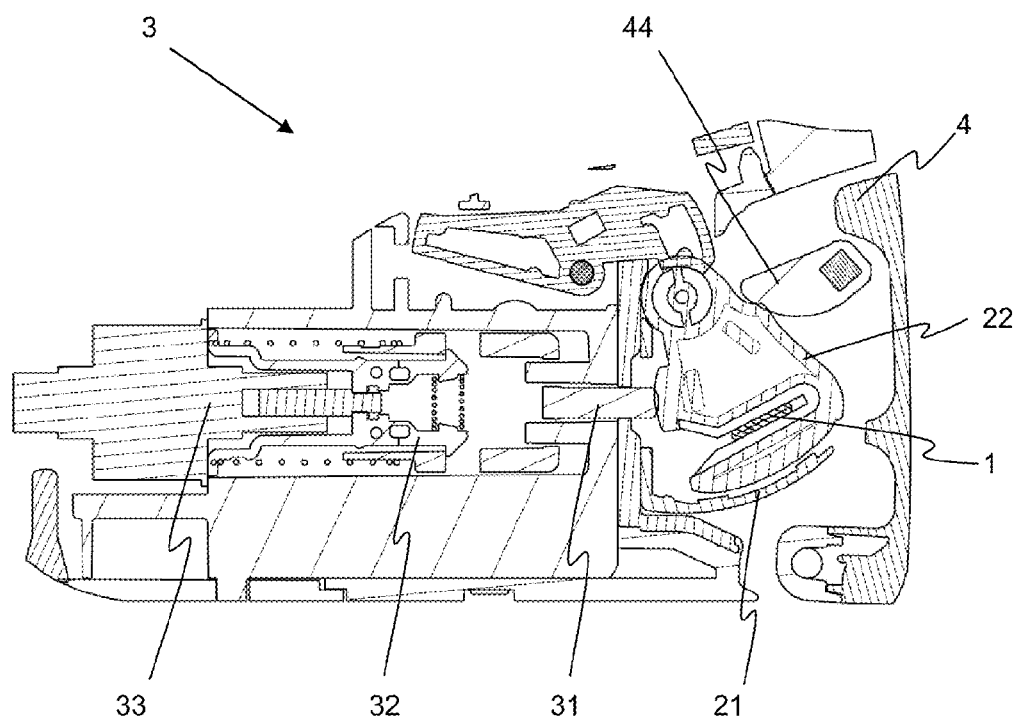
Figure 5:
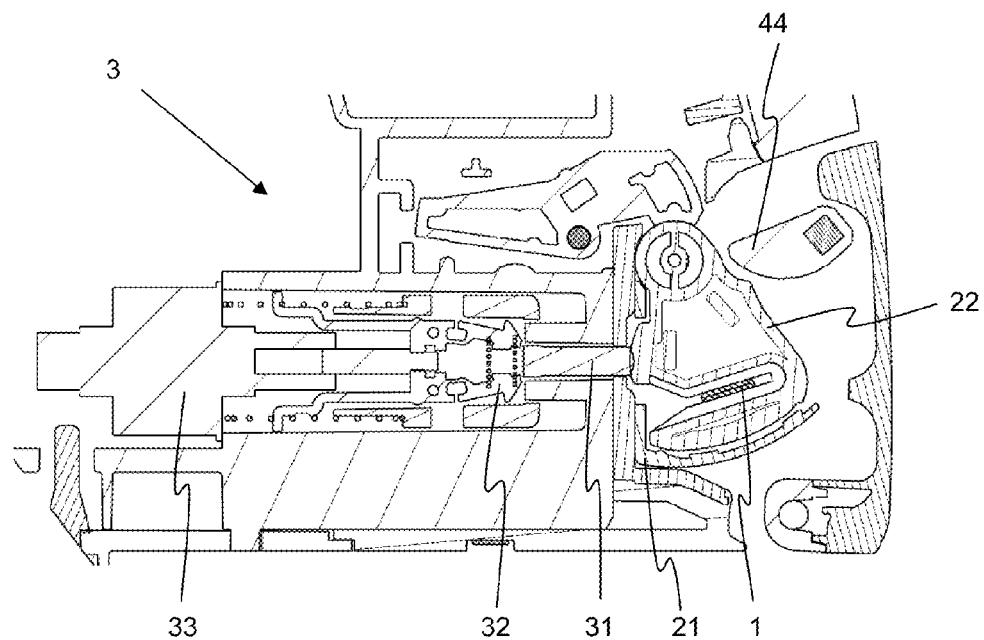
Figure 6:
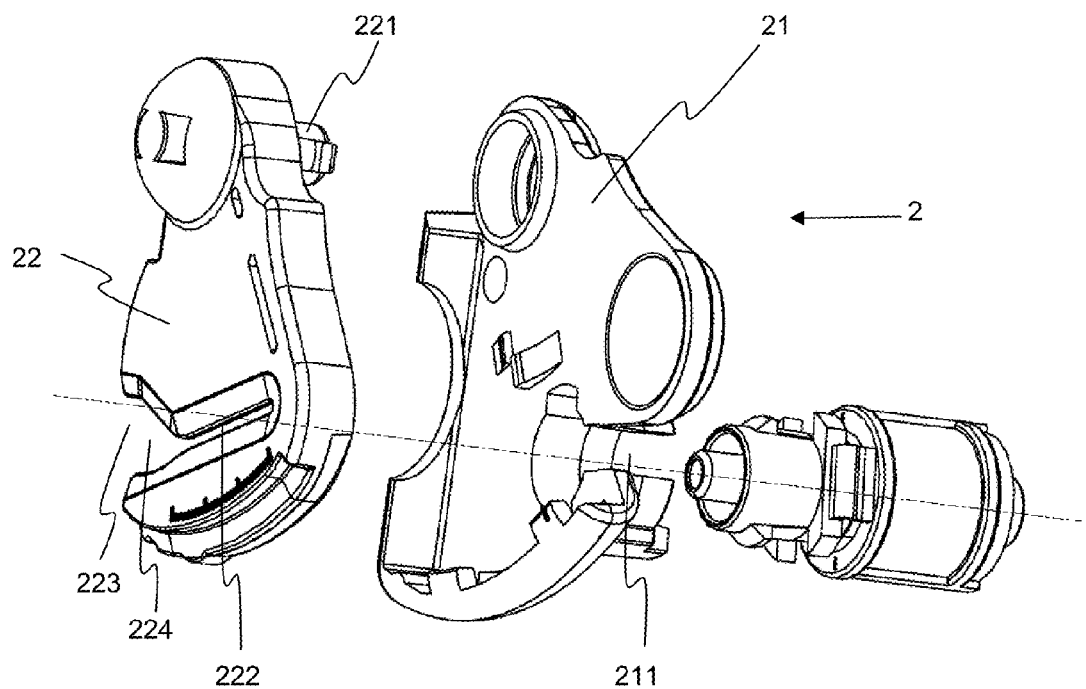
Figure 7:
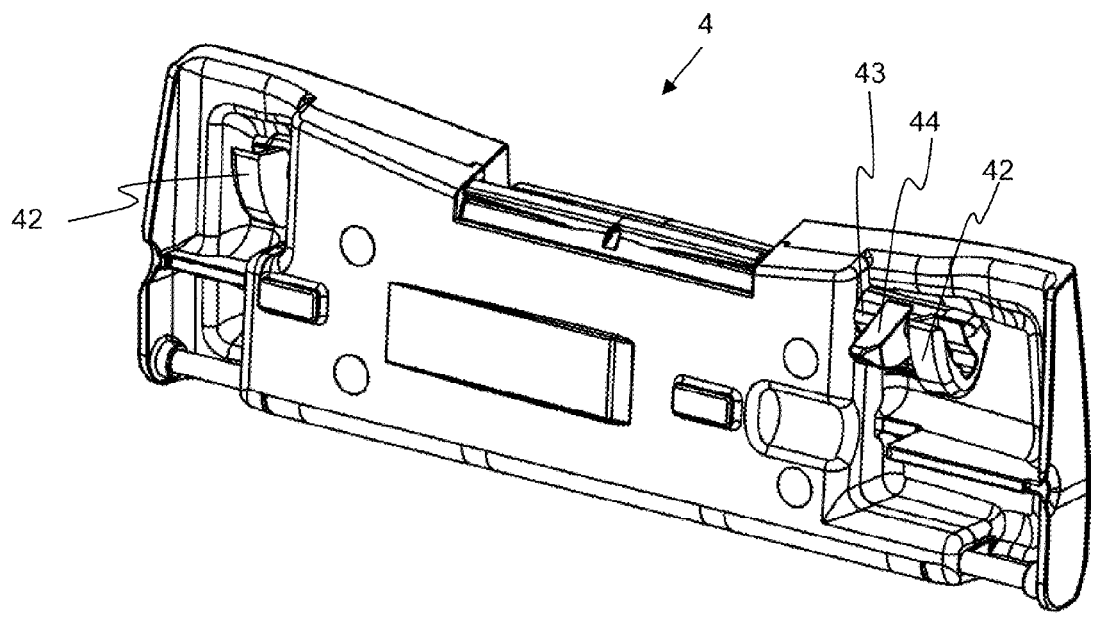
Figure 8:
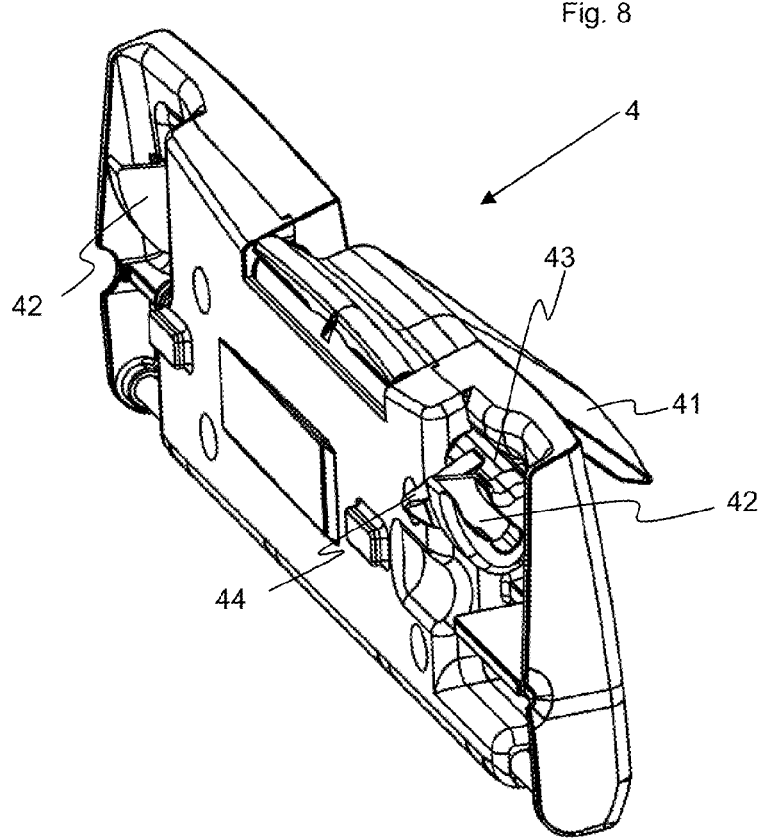
Figure 9:
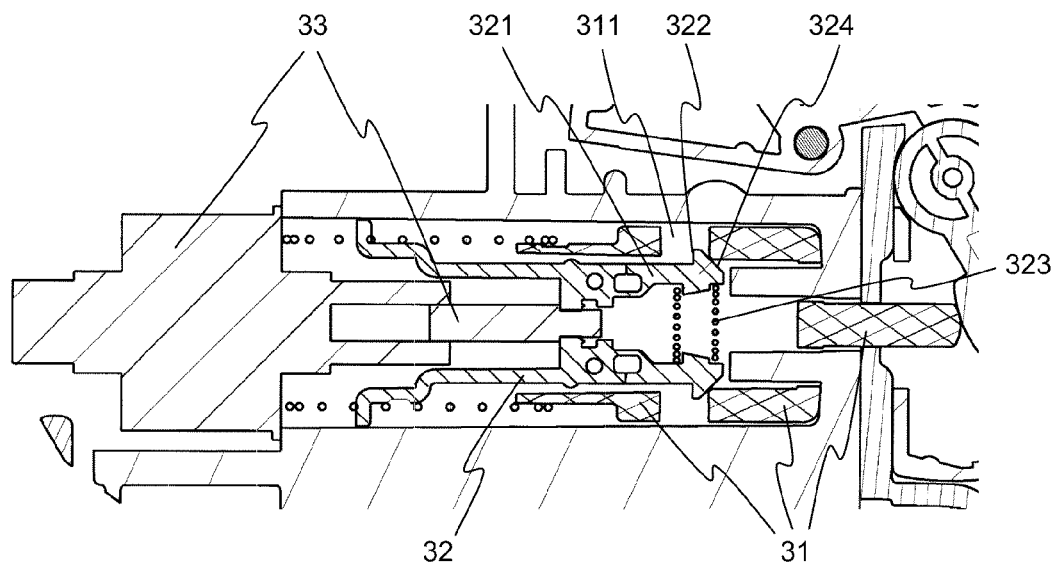

An example of an embodiment of the invention is described below with the help of the figures, which show:

FIG. 1: A sectional view through the pump housing at the moment the door is closed, which causes the clamp to close;

FIG. 2: A sectional view according to FIG. 1, with the door closed and the handle released, the clamp remaining closed;

FIG. 3: A sectional view according to FIG. 1, with the clamp being opened by the opening device;

FIG. 4: A sectional view according to FIG. 1, at the moment when the door is going to be opened, the handle being raised, which causes the clamp to close;

FIG. 5: A sectional view according to FIG. 1, in which the mechanical fuse tripped when an attempt to open the door occurred at the moment the clamp was going to be opened according to FIG. 3;

FIG. 6: An exploded perspective view of the elements of the clamp;

FIG. 7: A perspective view of the door;

FIG. 8: Another perspective view of the door;

FIG. 9: A sectional view of the mechanical fuse in the operating position; and

Figure 10:
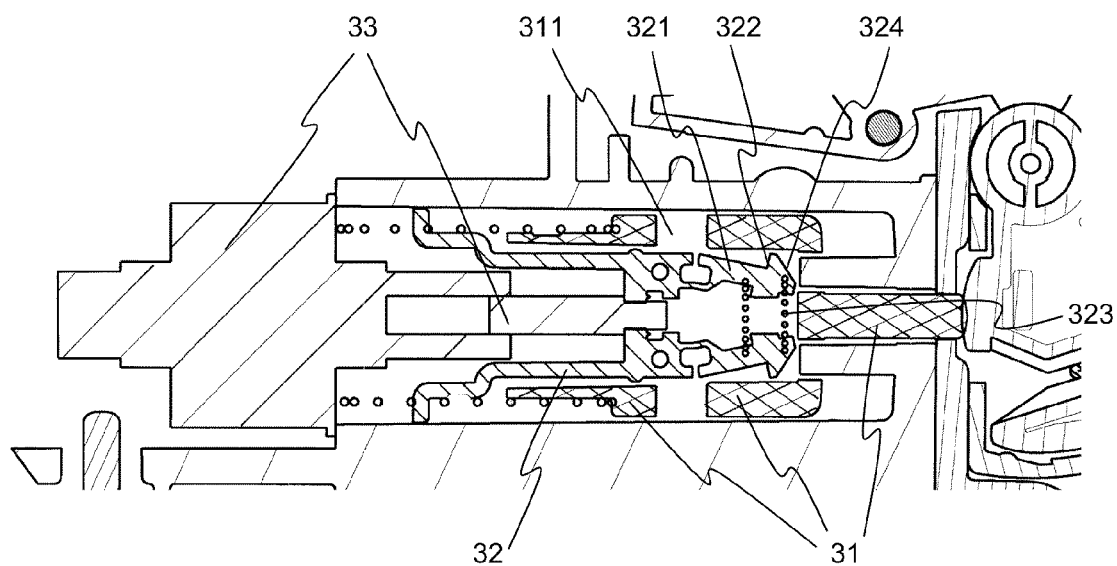

FIG. 10: A sectional view according to FIG. 9 of the mechanical fuse after it trips.

The device of the invention is made up primarily of a tube (1) going into a positive displacement pump (not shown) that can be closed or opened by a clamp (2). The pump and the clamp (2) are placed in a housing (3) that can be closed with a door (4).

In the example given here, we use a clamp known as a slide clamp, composed of two parts: a first, stationary part (21) and a mobile part (22). The tube (1) goes through a substantially cylindrical opening (211) whose particular function is to hold it in place radially. This stationary part is integral with the housing (3) and does not move. The mobile part (22), conversely, can pivot around a pivot pin (221) that can be accommodated in the stationary part (21) of the clamp (2), for example. This mobile part (22) is equipped with a slot (222) opening onto a wider part (223). The width of the slot (222) is chosen so that the tube (1) is flattened when it is engaged therein, and is thus obstructed. By contrast, the opening (223) is wide enough so that the tube (1) is nearly unrestricted when inside it, so that it returns substantially to its normal cylindrical shape, allowing the pumped liquid to go through. In practice, the tube is held in a slightly pinched shape, which makes it easier to insert in the slot (222). However, the opening (223) is wide enough so as to not interfere with the flow of the liquid. A transition section (224) makes it possible to move the tube from the unrestricted position in the opening (223) to the flattened position in the slot (222). This mobile part (22) of the clamp (2) can thus pivot from an open position in which its opening (223) is substantially aligned with the opening (211) of the stationary part, in which position the tube (1) is open, to a closed position in which the opening (211) of the stationary part is aligned with the slot (222) of the mobile part, in which position the flattened tube is closed. For example, FIG. 1 shows the closed position, while FIG. 3 shows the open position.

The closing of the clamp (2) is carried out by closure means attached onto the door (4). The door (4) is equipped with a handle (41) that must be pivoted to enable the door to open or close (4). Making the handle (41) pivot causes hooks to pivot (42). When the handle is in the stowed position, the hooks (42) hook into corresponding projections in the housing (3) that are not shown here, preventing the door (4) from opening unintentionally. When the handle (41) is in the pivoted position, the hooks (42) unhook from the projections, allowing the door to open (4). In order to do this, the handle is mounted on a pivot pin (43) on which the hooks (42) are also mounted. Besides these hooks (42) needed for opening and closing the door, the pivot pin (43) also has a cam (44) on it. This cam (44) can thus pivot as well, between a pivoted position where, when the door (4) is closed it causes the mobile part (22) of the clamp (2) to pivot shut, and a stowed position in which it no longer blocks the mobile part (22) shut. The pivoted position of the cam (44) can be seen in FIGS. 1, 4, 7 and 8, whereas the stowed position can be seen in FIGS. 2 and 3. The cam (44) thus serves as a closure means, both for closing the clamp when the door is made to close and for closing the clamp when the door is made to open. Likewise, the pivot pin (43) and the handle (41) form the means for making the door (4) open and close.

The clamp (2) is opened by a mobile finger (31) placed in the housing (3) and activated by a motor (33). Moving translationally, this finger (31) comes to bear on the face of the mobile part (22) of the clamp (2) opposite the face on which the cam (44) bears. This causes the mobile part (22) to pivot from its closed position into its open position. This mobile finger (31) associated with the motor (33) forms the means for making the clamp (2) open after the door has been closed.

The operating mode of the control device according to the invention is described below with reference to FIGS. 1 to 4. In order to close the door (4), the handle (41) must be raised so that the hooks (42) can move around the closure projections. Raising the handle causes the cam (44) to pivot. When the door is pushed into its closed position, the pivoted cam comes to bear on the face of the mobile part (22) of the clamp on the same side as the far end of the slot (222). This causes the mobile part (22) to pivot on its pivot pin (221), forcing the tube (1) into the slot (222). The tube, which is flattened inside the slot, is thus in the closed position. This is the position shown in FIG. 1.

As soon as the handle is stowed, the cam (44) and the hooks (42) return to their respective stowed positions, as shown in FIG. 2. The slot (222) is long enough so that the mobile part (22) cannot return to the open position without external aid.

Thus, the door (4) of the device is closed and the tube (1) occluded. Now it is possible, for example, to conduct an integrity test on the pump without administering any liquid to the patient. If the test result is favorable, the finger (31) is activated, causing the mobile part (22) of the clamp (2) to pivot into the open position. Since the handle (4) is stowed, the cam (44) does not impede this pivoting movement. This brings us to the position shown in FIG. 3. Once the pivoting movement is finished, the finger (31) returns to its initial position, which does not impede the reverse pivoting movement initiated by the cam (44).

If for some reason the door must be opened, the handle (41) must first be pivoted, which, firstly, causes the hooks (42) to pivot so that they can unhook from the projections, and secondly, causes the cam (44) to pivot, which in turn makes the mobile part (22) of the clamp (2) pivot. This brings us to the position shown in FIG. 4.

It is imperative to have the clamp in the closed position when the door is open. In other words, if for some reason someone opens the door at the exact moment when the finger (31) is moving translationally to make the mobile part (22) pivot into the open position, the movement to close the clamp (2) must have priority over the opposite movement to open it. Likewise, if the door is made to open when the finger (31) is in the extended position, the clamp (2) must be able to close regardless. In order to do this, provision is made to insert a mechanical fuse (32) between the motor and the finger (31), which gives way if the pressure required to move the finger (31) translationally is greater than a normal value. FIG. 5 shows an example of this kind. It can be seen that the cam (44) is in the pivoted position, preventing the mobile part (22) from returning to an open position. The mechanical fuse (32) has played its part, then, by giving way so that the motor was unable to drive the finger (31) translationally.

The operating mode of the mechanical fuse (32) is explained in more detail in FIGS. 9 and 10. The fuse (32) is equipped with hooks (321) that are held in their working position, seen in FIG. 9, by a spring (323) that serves to push them radially outward. These hooks (321) are normally engaged in notches (311) in the finger (31). This way, when the motor (33) initiates a leftward retraction, it drives the fuse (32) and the hooks (321) along with it. The hooks in turn drive the finger (31) due to the stops (322) located on top of them, which bear against the back ends (on the left in the figure) of the notches (311). This can be clearly seen in FIG. 4. Conversely, if the motor (33) initiates a rightward translational movement, it drives the fuse (32), and the hooks (321) along with it, which come to abut against the other end of the notches (311) in the finger (31), driving it in this general movement of rightward extension. This is what is shown in FIGS. 3 and 9.

If the cam (44) blocks the pivoting part (22) of the clamp (2) from moving, as in the example in FIG. 5, the hooks (321) then give way and pivot toward the center of the fuse (32) against the action of the spring (323) because of bevels (324) located on top of them on the face opposite the stops (322). The fuse ends up in the position shown in FIGS. 5 and 10. The opening means formed by the finger (31) are thus deactivated and can no longer make the clamp (2) open.

Likewise, if someone opens the door (4) when the finger (31) is still extended and the clamp (2) is in an open position as in FIG. 3, this causes the cam (44) to pivot, which stows the pivoting part (22) of the clamp (2) into the closed position. This in turn pushes the finger (31). Since the fuse (32) cannot back up because the motor (33) is not in the retracted position, it is the hooks (321) that give way, pivoting toward the center of the fuse (32) against the action of the spring (322). This is the position shown in FIGS. 5 and 10. Thus, the fuse has tripped. The opening means (31) are once again deactivated and cannot make the clamp (2) open.

Once the door is closed again, the fuse can automatically reset as soon as the motor (33) returns to its retracted position, e.g., shown in FIG. 1. The spring (323) pushes the hooks (321) back into the notches (311) of the finger (31) as soon as the fuse has backed up far enough.

The example of an embodiment given here uses a clamp in which the tube is pinched inside a pivotable slot. It follows that the slot can also have translational movement rather than pivoting. In addition, it is also quite possible to use a pinch clamp between two stops that can move relative to one another, whether translationally or pivotably.

The movement of the finger (31) does not necessarily have to be translational; it could very well be a pivoting movement, for example. Also, the electric motor can be replaced with a manual action or a mechanical device.

As well as ensuring that the tube is always closed when the door is in the open position, the safety device of the invention also ensures that the tube remains closed once the door is closed as long as a suitable device has not made the clamp open. This entirely mechanical closure device is not subject to the hazards of a potentially faulty power supply.

References
1 Tube
2 Clamp
  21 Stationary part
    211 Cylindrical opening
  22 Mobile part
    221 Pivot pin
    222 Slot
    223 Opening
    224 Transition section
3 Pump housing
  31 Finger
    311 Notches
  32 Mechanical fuse
    321 Hooks
    322 Stop
    323 Spring
    324 Bevel
  33 Motor
4 Door
  41 Handle
  42 Hooks
  43 Handle pivot pin
  44 Cam

The invention claimed is:

1. Method for controlling the opening and closing of a clamp intended to seal a flexible tube placed inside a housing that can be closed with a door, the clamp being placed in the housing and cooperating with the tube in order to open the tube in an open position of the clamp and seal the tube in a closed position of the clamp, said method comprising:
closing the door from an open position of the door to a closed position of the door, wherein, when the door passes from the open position of the door to the closed position of the door, the door causes the clamp to pass from the open position of the clamp to the closed position of the clamp.

2. Method according to claim 1, comprising:
opening the door from the closed position of the door to the open position of the door, wherein, when the door passes from the closed position of the door to the open position of the door, the door causes the clamp to pass from the open position of the clamp to the closed position of the clamp.

3. Method according to claim 1, comprising, after the door has been closed, reopening the clamp only after a predetermined event has occurred.

4. Method according to claim 3, comprising reopening the door before or at the moment of the predetermined event without reopening the clamp.

5. Device for controlling the opening and closing of a clamp intended to seal a flexible tube, in particular, in a positive displacement pump comprising, among other things,
a housing that can be closed with a door,
a tube placed inside the housing, and
a clamp placed inside the housing and cooperating with the tube in order to open the tube in an open position of the clamp and seal the tube in a closed position of the clamp, and
means for closing the clamp by closing the door from an open position of the door to a closed position of the door, wherein, when the door passes from the open position of the door to the closed position of the door, the door causes the clamp to pass from the open position of the clamp to the closed position of the clamp.

6. Device according to claim 5, wherein means are provided for closing the clamp when the door is made to open, wherein, when the door passes from the closed position of the door to the open position of the door, the door causes the clamp to pass from the open position of the clamp to the closed position of the clamp.

7. Device according to claim 6, wherein the means for closing the clamp when the door is made to open and the means for closing the clamp when the door is made to close are identical.

8. Device according to claim 5, wherein the means for closing the clamp when the door is made to close are activated by means for making the door open or close.

9. Device according to claim 8, wherein the means for making the door open or close comprise a handle that is operable from the outside of the housing.

10. Device according to claim 8, wherein the means for closing the clamp when the door is made to close comprise a cam that cooperates with the means for making the door open or close.

11. Device according to claim 10, wherein the means for making the door open or close comprise a handle, and the cam is integral with a pivot pin of the handle.

12. Device according to claim 6, wherein the clamp is a slide clamp, said slide clamp comprising a stationary part and a mobile part, and wherein the means for closing the clamp when the door is made to close are proportioned so as to make the mobile part of the slide clamp slide with respect to the stationary part.

13. Device according to claim 5, comprising means for making the clamp open after the door has been closed.

14. Device according to claim 13, comprising control means for activating the means for making the clamp open so as to open the clamp when a certain event has occurred.

15. Device according to claim 14, wherein the control means activate the means for making the clamp open so as to open the clamp after a system integrity test has been conducted.

16. Device according to claim 13, wherein a mechanical fuse is provided for deactivating the means for making the clamp open so as to prevent the clamp from opening in the event that the door is made to open at the moment the means for making the clamp open are activated.

17. Device according to claim 5, which additionally comprises a positive displacement pump connected to the tube.

18. Device according to claim 17, wherein the positive displacement pump is a peristaltic pump.

19. Device according to claim 17, wherein the positive displacement pump is placed upstream of the clamp.

20. Device according to claim 12, wherein the mobile part of the slide clamp has rotational mobility with respect to the stationary part.

21. Method according to claim 3, comprising, after the door has been closed, reopening the clamp only after an integrity test has been successfully conducted.

22. Device according to claim 6, wherein the means for closing the clamp when the door is made to open are activated by means for making the door open or close.

23. Device according to claim 22, wherein the means for making the door open or close comprise a handle that is operable from the outside of the housing.

24. Device according to claim 22, wherein the means for closing the clamp when the door is made to close comprise a cam that cooperates with the means for making the door open or close.

25. Device according to claim 24, wherein the means for making the door open or close comprise a handle, and the cam is integral with a pivot pin of the handle.

26. Device according to claim 6, wherein the clamp is a slide clamp, said slide clamp comprising a stationary part and a mobile part, and wherein the means for closing the clamp when the door is made to open are proportioned so as to make the mobile part of the slide clamp slide with respect to the stationary part.

27. Device according to claim 26, wherein the mobile part of the slide clamp has rotational mobility with respect to the stationary part.

28. Method according to claim 1, wherein, when the door passes from the open position of the door to the closed position of the door, the door bears mechanically on the clamp so that the clamp passes from the open position of the clamp to the closed position of the clamp.

29. Method according to claim 28, wherein the door comprises closure means for closing the clamp when the door is made to close, wherein, when the door passes from the open position of the door to the closed position of the door, the closure means bears mechanically on the clamp so that the clamp passes from the open position of the clamp to the closed position of the clamp.

30. Device according to claim 5, wherein, when the door passes from the open position of the door to the closed position of the door, the closure means bears mechanically on the clamp so that the clamp passes from the open position of the clamp to the closed position of the clamp.

* * * * *